United States Patent [19]

Rutloh

[11] Patent Number: 4,497,211
[45] Date of Patent: Feb. 5, 1985

[54] CIRCUIT FOR GENERATING SAWTOOTH SHAPED PULSES FOR ULTRASONIC INSTRUMENTS

[75] Inventor: Max Rutloh, Erfstadt, Fed. Rep. of Germany

[73] Assignee: Krautkramer-Branson, Inc., Lewistown, Pa.

[21] Appl. No.: 492,748

[22] Filed: May 9, 1983

[30] Foreign Application Priority Data

Jul. 17, 1982 [EP] European Pat. Off. ........ 82106466.4

[51] Int. Cl.³ .......................................... G01N 29/04
[52] U.S. Cl. ...................................... 73/606; 73/611; 73/620
[58] Field of Search ................ 73/606, 607, 611, 614, 73/620, 629; 328/185

[56] References Cited

U.S. PATENT DOCUMENTS

| | | | |
|---|---|---|---|
| 2,975,416 | 3/1961 | Mack et al. | 328/185 |
| 3,323,353 | 6/1967 | Munger | 328/185 |
| 3,571,755 | 3/1971 | Ejiri | 328/185 |
| 3,577,007 | 5/1971 | Cross | 328/185 |
| 4,064,742 | 12/1977 | Pittaro | 73/611 |
| 4,373,394 | 2/1983 | Renzel et al. | 73/606 |

FOREIGN PATENT DOCUMENTS

1462739 12/1968 Fed. Rep. of Germany .

OTHER PUBLICATIONS

D. M. Brockman, Synchronous Ramp Generator Maintains Output Linearity, *Electronics*, Jan. 18, 1973, p. 170.
A. G. Golovko et al., An Adjustable Sawtooth-Voltage Generator, *Instruments and Experimental Techniques*, vol. 10, No. 2, Jan.–Feb., 1975, pp. 185-88.
S. Picard, Circuit Allowing Oscilloscopes to be Automatically Adjusted, *IBM Technical Disclosure Bulletin*, vol. 24, No. 7A, Dec. 1981.
G. Jeansaume, Synthétiseur de fréquence en CMOS, *Electronique et Application Industrielle*, No. 254, Jun. 1978, pp. 45-47.

Primary Examiner—Stephen A. Kreitman
Assistant Examiner—John E. Chapman, Jr.
Attorney, Agent, or Firm—Ervin B. Steinberg; Philip J. Feig

[57] ABSTRACT

A circuit for adjusting the sweep time provided by a sweep generator used in an ultrasonic test instrument is described. The adjustment takes into account three test parameters, i.e. the angle of propagation of the sound in the workpiece, the speed of propagation of sound in the workpiece, and the thickness of the workpiece. To this end, the quartz-stabilized frequency of an oscillator comprising an adjustable frequency divider is divided by the angle function value of the angle of sound propagation to which the test instrument is set. The divided frequency is fed to a frequency multiplier in a phase locked loop circuit, comprising an adjustable frequency divider by means of which the speed of propagation of the sound is adjusted. A succeeding time reference stage contains also an adjustable frequency divider by means of which the workpiece thickness is adjusted. The duration of rectangular pulses generated by the time reference stage takes into account the three adjusted parameters with the same relative accuracy as that preset by the quartz-stabilized oscillator. The duration of the rectangular pulse generated by the time reference stage is equal to the sweep time.

7 Claims, 4 Drawing Figures

CIRCUIT FOR GENERATING SAWTOOTH SHAPED PULSES FOR ULTRASONIC INSTRUMENTS

BRIEF SUMMARY OF THE INVENTION

This invention relates to a circuit for generating sawtooth shaped pulses of adjustable sweep time, in which a sweep generator comprising a voltage-dependent constant current source, an integrating circuit and a comparator circuit, is triggered by pulses from a trigger. The invention also relates to the use of such a circuit in ultrasonic measuring instruments used for the nondestructive testing of materials.

A circuit of this kind is known, for example see U.S. Pat. No. 3,577,007 issued to A. L. Cross dated May 4, 1971, wherein the voltage at the sweep circuit capacitors is integrated and compared with a set value in a comparator during a preset trigger time. In the event of a deviation from the set value, the difference voltage causes the constant current source to be controlled so that the sweep time, i.e. the duration of the sawtooth pulse portion used for the line deflection, remains approximately constant.

A disadvantage of the prior circuit is that the control range of the sweep time is substantially restricted because only a single capacitor is used. Furthermore, the flyback time of the sawtooth pulses cannot be made arbitrarily short because the comparison between the set value and the actual value occurs during that time.

U.S. Pat. No. 4,373,394 issued to P. Renzel and dated Feb. 15, 1983 also discloses a circuit for generating sawtooth pulses for ultrasonic instruments. In this disclosure the sweep time can be controlled to exhibit a constant value by means of digital circuit components. The comparison between the set value and the actual value preferably is carried out by means of a microprocessor.

A limitation of this latter circuit resides in the fact that there is a relatively long time period between the adjustment of the sweep time and the resulting occurrence of the sawtooth pulse because the components used usually do not operate sufficiently fast. Alternatively, components which operate fast are expensive, e.g. A/D converters.

An object of this invention is to provide a simple, accurate and rapidly operating circuit of the kind referred to hereinbefore.

Specific advantages of the present invention reside in the feature that parameter values can be inputted separately without the use of calibrating means. A rectangular pulse defining the sweep time can also be stabilized by a frequency-stabilized pulse generator (quartz stabilization of sweep time), and simple and inexpensive embodiments without the use of microprocessors or A/D converters.

Other advantages and details of the invention will be apparent from the following description when taken in conjunction with the accompanying drawings.

DETAILED DESCRIPTION OF THE INVENTION

Figure 1:
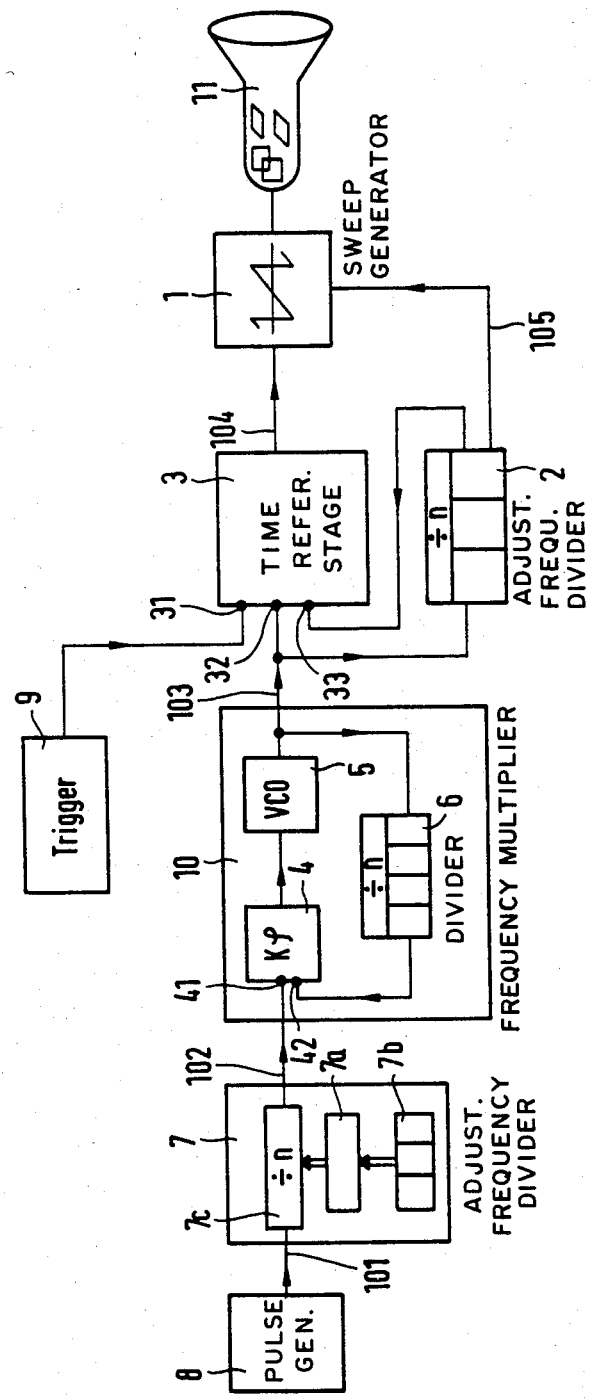
FIG. 1 is a schematic block diagram of one exemplified embodiment of the invention.

FIG. 1 illustrates one exemplary embodiment of the invention. Reference numeral 1 denotes a sweep generator for generating sawtooth shaped pulses for the time deflection axis of the cathode ray tube 11. The sweep generator 1 is preceded by a time reference stage 3 which generates rectangular pulses, the duration of which is equal to a set value for the sweep time. Trigger circuit 9 is connected to a first input 31 of the time reference stage 3. A frequency multiplier 10, which is referred to as the second frequency-transforming means, is connected to a second input 32 of the time reference stage 3.

In this embodiment, frequency multiplier 10 consists of a phase comparator 4 followed by a voltage-controlled oscillator 5. The frequency signals generated by the latter are fed to a first adjustable frequency divider 6 and the divided frequency is fed back to the phase comparator (input 42). This frequency multiplier circuit is known per se as phase locked loop (PLL). A second adjustable frequency divider 2 is also connected to the second input 32 of time reference stage 3 and feeds the divided frequency back to the time reference stage 3 at input connection 33.

A third adjustable frequency divider 7, referred to as the first frequency-transforming means, is connected by conductor 102 to the input of the frequency multiplier 10. In one preferred embodiment, this third adjustable frequency divider consists of a coding switch 7b for the selection of numerical values, a constant store 7a which converts the mathematical equations (e.g. trigonometric function values for selected angles) corresponding to numerical values selected by the coding switch 7b into ratios for the actual frequency dividing circuit 7c. A frequency stabilized pulse generator 8 is connected by conductor 101 to the input of this third adjustable frequency divider 7.

Figure 2:
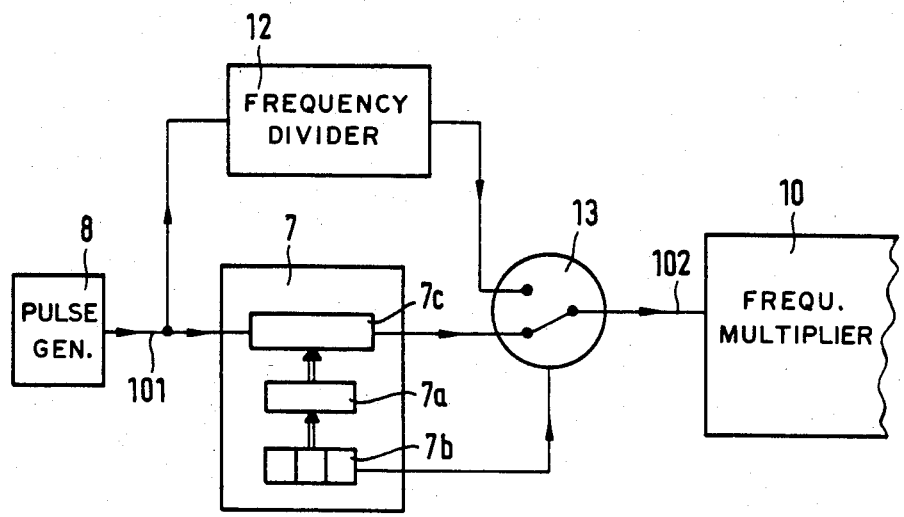
FIG. 2 is a block diagram showing the use of an additional frequency divider set to a fixed value.

As shown in FIG. 2, a frequency divider 12 set to a fixed value can be connected in parallel with the third adjustable frequency divider 7 so that the adjustable frequency divider 7 is replaced by the fixed frequency divider 12 at a specific numerical value, set by means of the coding switch 7b. This change-over is effected, for example, by means of the electronic selector switch 13.

Figure 3:
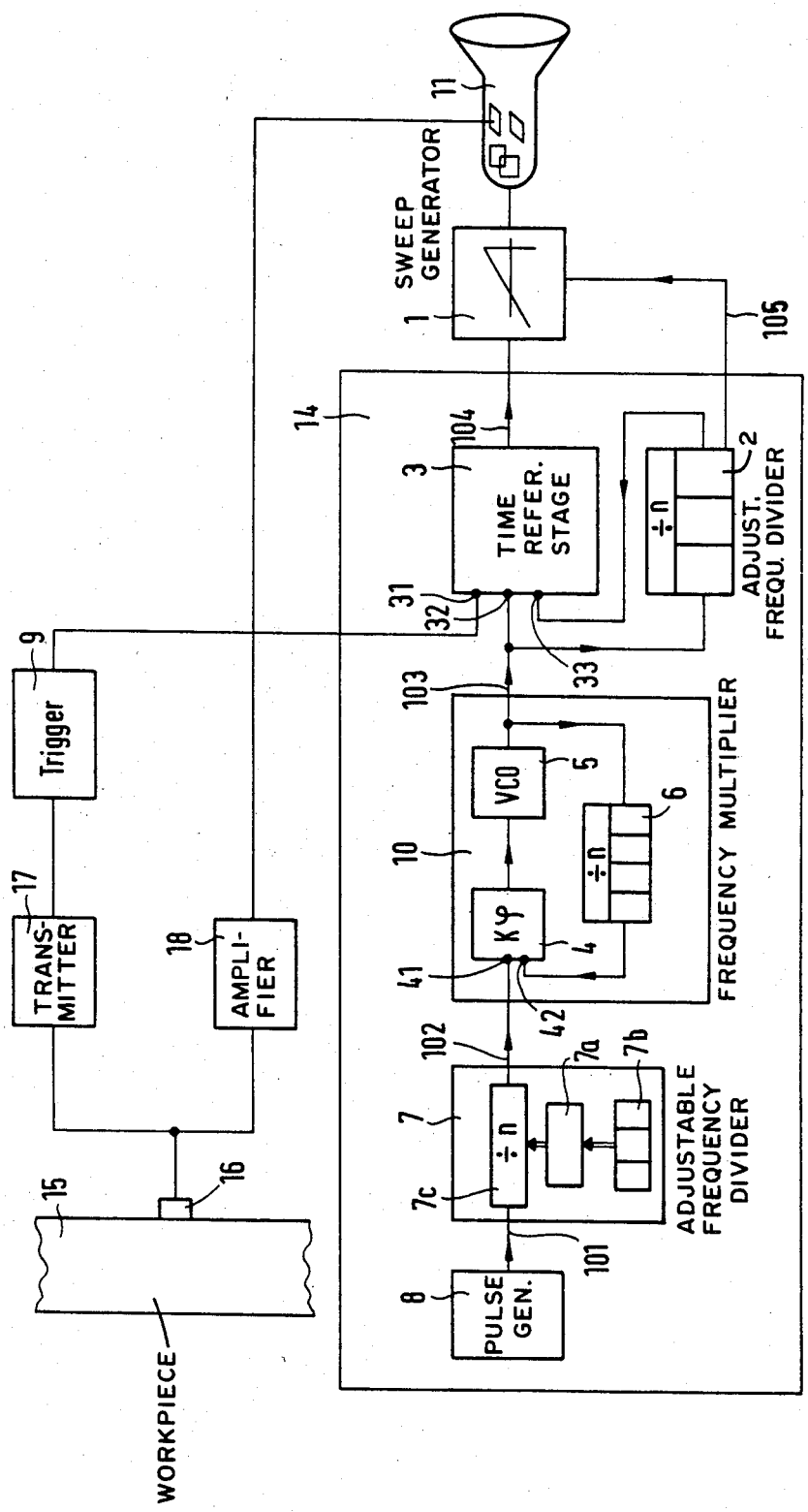
FIG. 3 is a schematic block diagram showing the use of the circuit arrangement according to the invention in conjunction with an ultrasonic test instrument.

A preferred example of using the circuit per FIG. 1 in conjunction with an ultrasonic test instrument is shown in FIG. 3. The circuit shown in FIG. 1 comprising the blocks 2, 3, 7, 8 and 10 is combined in block 14 in FIG. 3 in the form of an adjustable value setting means for the sweep time. In addition to this circuit 14, a workpiece 15 is illustrated with an acoustically coupled ultrasonic test probe 16. The probe when energized by transmitter 17 transmits ultrasonic pulses into the workpiece 15. The probe 16 also receives the ultrasonic signals reflected from the workpiece and converts them into echo responsive electrical signals. The latter signals are amplified in an amplifier 18 and fed to the vertical deflection plates of cathode ray tube 11. The trigger 9 triggers both the ultrasonic transmitter 17 and the circuit 14, which determines the sweep time for generating the sawtooth pulse in the sweep generator 1. Other components of a conventional ultrasonic test instrument are not shown.

The function of the circuit according to FIGS. 1 and 2 will be described in detail with reference to FIG. 3. To simplify the mode of operation, it will be assumed that the trigger 9 simultaneously triggers the transmission pulse in transmitter 17 and the start of the sweep time.

Figure 4:
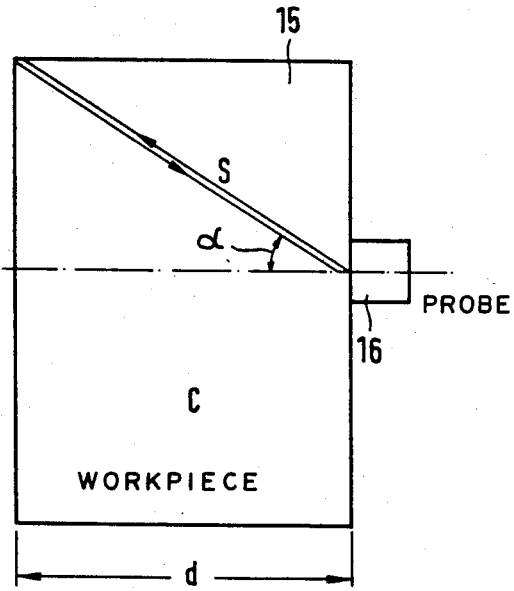
FIG. 4 is an explanatory sketch showing a workpiece with an ultrasonic test probe and the parameters which are to be adjusted for the test.

In this description of the function, the sweep time of the sawtooth pulse for the time deflection is required to correspond to the transit time of the ultrasonic pulse workpiece 15. This sweep time, however, is dependent on the speed of propagation "c" of sound in the workpiece material, the thickness "d" of the workpiece, and the angle of propagation of the sound "α". FIG. 4 illustrates these parameters, and it must be kept in mind that in the pulse echo technique the sound traverses a distance in the workpiece both in the forward and in the reverse direction, i.e. twice. The sweep time therefore must be adjusted to three parameters, i.e. angle α, speed of propagation of sound "c" and workpieces thickness "d" in accordance with the equation:

$$t = 2s/c = 2d/c \cdot \cos \alpha$$

In describing the function it is advantageous to start with the pulse generator 8. The latter, preferably a quartz-stabilized pulse generator, generates rectangular pulses having a period of 184 μs, for example, corresponding to a frequency of about 5.435 kHz. These pulses are fed via conductor 101 to the frequency divider referred to as the third adjustable frequency divider 7. In the latter, these pulses are changed in respect of their time duration in accordance with the cosine of the angle of propagation α. Adjustment of the angle of propagation can be provided by a three-digit coding switch 7b, it being sufficient in practice for the angles to be graduated in 0.5° steps. The values of the angle functions are called up from a permanently stored data store 7a and fed to the frequency divider circuit unit 7c. If, for example, the angle of propagation is changed from 30.0° to 80.0°, the pulse duration must be varied by the ratio cos 30.0°/cos 80° ≈ 5:1, i.e. the frequency must be varied by a ratio of 1:5. For an angle of propagation 0°, i.e. vertical incidence, the value cos α=1 must be taken into account in the adjustable frequency divider 7.

In this typical embodiment, the frequency of 5.435 kHz on conductor 101 for the angle of propagation 0° must first be divided by a basic factor of 45 to obtain a frequency of 121 Hz. The frequency of 121 Hz, which corresponds to a period of 8.28 ms, is thus available for this angle of propagation on conductor 102, i.e. at the output of adjustable frequency divider 7. For an angle of propagation of 30° along conductor 102 there will be a frequency 121 Hz×cos 30° = 104.6 Hz, corresponding to a period of 9.56 ms, while for an angle of propagation of 80° the frequency is 121 Hz×cos 80° = 21 Hz, corresponding to a period of 48 ms. The angle of propagation is thus taken into account as a first adjustable parameter in the pulse frequency on conductor 102, i.e. at the input to the frequency multiplier 10 and in the period of these pulses.

In frequency multiplier 10 a pulse train of a higher frequency is generated along conductor 103 from the pulse trains along input conductor 102. In accordance with the operation of PLL frequency multipliers, this higher frequency is higher than the frequency along conductor 102 at the input to the frequency multiplier by an amount equal to the frequency division ratio of the adjustable frequency divider 6. The value of this higher frequency will be apparent from the following description.

For an angle of propagation of 0°, a speed of propagation of sound of 8,000 m/s, and a measuring range of 5 mm, corresponding to a pulse transit distance of 10 mm, the sweep time requires a pulse period along conductor 103 equal to $t = 10 \times 10^{-3}$ m/8,000 m/s = 1.25 μs. For a speed of propagation of sound of 2,000 m/s the pulse period required for the same pulse distance is 5 μs. For the other angles of propagation the pulse times are longer by amounts corresponding to cos α. These are already provided by the frequency divider 7 as described. The speed of propagation of sound applicable to the workpiece can be adjusted by means of the adjustable frequency divider 6 in the frequency multiplier 10. In the present example the velocity can be adjusted between 2,000 m/s and 8,000 m/s to an accuracy of 1 m/sec, i.e. 4-digits. Conductor 103 accordingly carries a pulse period which already allows for two parameters, i.e. the angle of propagation and the speed of sound propagation. The pulse trains with the frequencies and periods determined in this way are fed to the time reference stage 3. The stage 3 starts a d.c. pulse in response to each trigger signal produced by trigger 9, and ends such d.c. pulse after termination of the period of the pulse at the output of the frequency multiplier 10 manifest along condutor 103.

Synchronization of the leading edge of the d.c. pulse by the trigger pulse is effected in the manner known in connection with cathode ray tube oscilloscopes. This d.c. pulse is fed to the sweep generator 1. For adjustment of the third parameter, the pre-settable workpiece thickness range, the pulse train along conductor 103 is fed to another frequency divider referred to as the second adjustable frequency divider 2. For the 5 mm measuring range, the divider ratio in this example is 1:1 while for a 5 m measuring range the ratio is 1:1,000, so that the period of the pulses on conductor 103 can be varied in this ratio. The pulses along conductor 104, i.e. those fed to the sweep generator 1, accordingly take into account this third parameter. In this example the frequency divider 2 is constructed so that a pulse train along conductor 103 is fed to the sweep generator 1 without any division on each trigger operation for a measuring range of 5 mm, while for a measuring range of 5 m the sweep time is longer by a factor of 1,000 as a result of the frequency division.

The following table indicates typical limits with regard to the selection of the adjustment of the three parameters:

| Angle of Propagation | Speed of Propagation of Sound | Measuring Range | |
|---|---|---|---|
| | | mm | m |
| 1° | 3.000 m/s | 25 μs | 25 ms |
| | 2.000 m/s | 5 μs | 5 ms |
| 30° | 3.000 m/s | 44 μs | 44 ms |
| | 2.000 m/s | 77 μs | 77 ms |
| 80° | 3.000 m/s | 1.2 μs | 1.2 ms |
| | 2.000 m/s | 3.8 μs | 3.8 ms |

In the case of the adjustable divider ratio of 1:1,000 for the adjustable frequency divider 2 and the resulting change of the sweep time by the same ratio, the voltage controlled constant current source in the sweep generator 1 would also have to control the current for the sweep capacitors in the same ratio. To obviate the associated difficulties, it is advantageous to switch the sweep capacitors when the division ratio of frequency divider 2 is changed, and this is done via conductor 105 in a manner known.

Since the angle of propagation used in ultrasonic testing is generally either vertical (0° angle of propagation) or angles between 30° and 80°, it is advantageous, as shown in FIG. 2, to design the adjustable frequency divider 7 only for angle functions of angles between 30° and 80° and accordingly to store only those values in the store 7a. For the 0° angle of propagation (vertical incidence), a selector switch 13, preferably an electronic switch, e.g. an OR gate, is switched to the fixed frequency divider 12 whenever the 0° angle is selected.

What is claimed is:

1. An ultrasonic test instrument for testing workpieces having a cathode ray tube for displaying ultrasonic signals and including a sweep generator for producing sawtooth signals for the time axis of said ultrasonic signals; the sweep time of said sawtooth signals being adjustable by a voltage controlled constant current source, and said sweep generator being responsive to trigger signals from a trigger generator, the improvement comprising:

a time reference stage for producing rectangularly shaped pulses, the duration of which is commensurate with the sweep time of said sawtooth signals, coupled to the input of said sweep generator;

an input of said time reference stage coupled for receiving said trigger signals from said trigger generator for causing the start of said rectangularly shaped pulses to be responsive to the receipt of said trigger signals, and a frequency stabilized pulse generator coupled serially with a frequency transforming means to another input of said time reference stage for providing signals which, except for a constant factor, terminate said rectangularly shaped pulses.

2. An ultrasonic test instrument as set forth in claim 1, said frequency transforming means comprising a third adjustable frequency divider and/or fixed frequency divider.

3. An ultrasonic test instrument as set forth in claim 1, said frequency transforming means comprising an adjustable frequency multiplier.

4. An ultrasonic test instrument as set forth in claim 2 or 3, said frequency transforming means comprising a first and a second serially coupled frequency transforming means; said first transforming means coupled to the output of said frequency stabilized pulse generator; said third adjustable frequency divider and/or said fixed frequency divider serving for adjusting a frequency value commensurate with the angle of propagation of sound in a workpiece to be tested, and said second frequency transforming means serving for adjusting a frequency commensurate with the speed of sound in the workpiece.

5. An ultrasonic test instrument as set forth in claim 2, said third adjustable frequency divider comprising a coding switch for selecting angles of sound propagation; a store coupled to said coding switch for providing signals commensurate with the trigonometric value of selected angles, and a frequency dividing circuit for receiving said signals commensurate with the trigonometric values.

6. An ultrasonic test instrument as set forth in claim 3, said adjustable frequency multiplier comprising a phase comparator coupled with one input to the signal from said frequency stabilized oscillator; a voltage controlled oscillator coupled with its input to the output from said phase comparator; the output of said voltage controlled oscillator coupled to one input of said time reference stage; and a frequency divider coupled for receiving the output from said voltage controlled oscillator and providing a signal to another input of said phase comparator.

7. An ultrasonic test instrument as set forth in claim 1, said time reference stage comprising a second adjustable frequency divider for causing the duration of the sweep time of said sawtooth signals to be commensurate with the range of the thickness of a workpiece to be measured.

* * * * *